United States Patent
Sharma et al.

(10) Patent No.: US 8,883,515 B2
(45) Date of Patent: Nov. 11, 2014

(54) APPARATUS, SYSTEM, AND METHOD OF PROCESSING BIOPSY SPECIMEN

(75) Inventors: Shree G. Sharma, Little Rock, AR (US); Manisha Singh, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 929 days.

(21) Appl. No.: 13/035,981

(22) Filed: Feb. 27, 2011

(65) Prior Publication Data

US 2012/0220044 A1  Aug. 30, 2012

(51) Int. Cl.
| | |
|---|---|
| G01N 1/28 | (2006.01) |
| G01N 1/30 | (2006.01) |
| B01L 3/02 | (2006.01) |
| B01L 3/00 | (2006.01) |
| G01N 1/31 | (2006.01) |
| G01N 1/10 | (2006.01) |
| G01N 35/02 | (2006.01) |
| G01N 35/00 | (2006.01) |

(52) U.S. Cl.
CPC .. G01N 1/30 (2013.01); G01N 1/31 (2013.01); G01N 1/10 (2013.01); G01N 35/02 (2013.01); G01N 35/0099 (2013.01); G01N 2001/315 (2013.01); B01L 3/0275 (2013.01); B01L 3/5082 (2013.01); B01L 2300/0618 (2013.01); B01L 2300/0681 (2013.01); B01L 2300/0851 (2013.01)
USPC .......................................................... 436/174

(58) Field of Classification Search
CPC ............ G01N 1/30; G01N 1/31; G01N 1/312
See application file for complete search history.

(56) References Cited

U.S. PATENT DOCUMENTS

| | | | |
|---|---|---|---|
| 4,801,553 A | 1/1989 | Owen et al. | |
| 5,260,872 A | 11/1993 | Copeland et al. | |
| 5,424,040 A | 6/1995 | Bjornsson | |
| 5,814,276 A | 9/1998 | Riggs | |
| 5,851,491 A * | 12/1998 | Moulton ........................ | 422/535 |
| 7,156,814 B1 | 1/2007 | Williamson, IV et al. | |
| 7,387,216 B1 * | 6/2008 | Smith ........................ | 220/254.3 |
| 8,485,987 B2 * | 7/2013 | Videbaek et al. ............. | 600/564 |
| 2001/0051365 A1* | 12/2001 | Morales et al. ............. | 435/173.4 |
| 2008/0027353 A1* | 1/2008 | Kliman ........................ | 600/562 |
| 2012/0183950 A1* | 7/2012 | Nicholas et al. .................. | 435/5 |

OTHER PUBLICATIONS

Grimm, E.E., and Schmidt, R.A., Reengineered Workflow in the Anatomic Pathology Laboratory, Archives of Pathology & Laboratory Medicine, Apr. 2009, 601-604, vol. 133, United States.

* cited by examiner

*Primary Examiner* — Christopher A Hixson
(74) *Attorney, Agent, or Firm* — Richard Blakely Glasgow

(57) ABSTRACT

A biopsy pipette with a filter attached in an internal compartment of a pipette designed to prevent lodging and possible loss of the tissue specimen for analysis. A biopsy test tube may be provided with a biopsy bag attached in the internal compartment of the test tube. Further, a biopsy cassette may be provided with an opening configured to receive a pipette. An automated and non-automated system and method of using the biopsy pipette, biopsy test tube, and biopsy cassette in the processing of biopsy specimen is also disclosed.

10 Claims, 8 Drawing Sheets

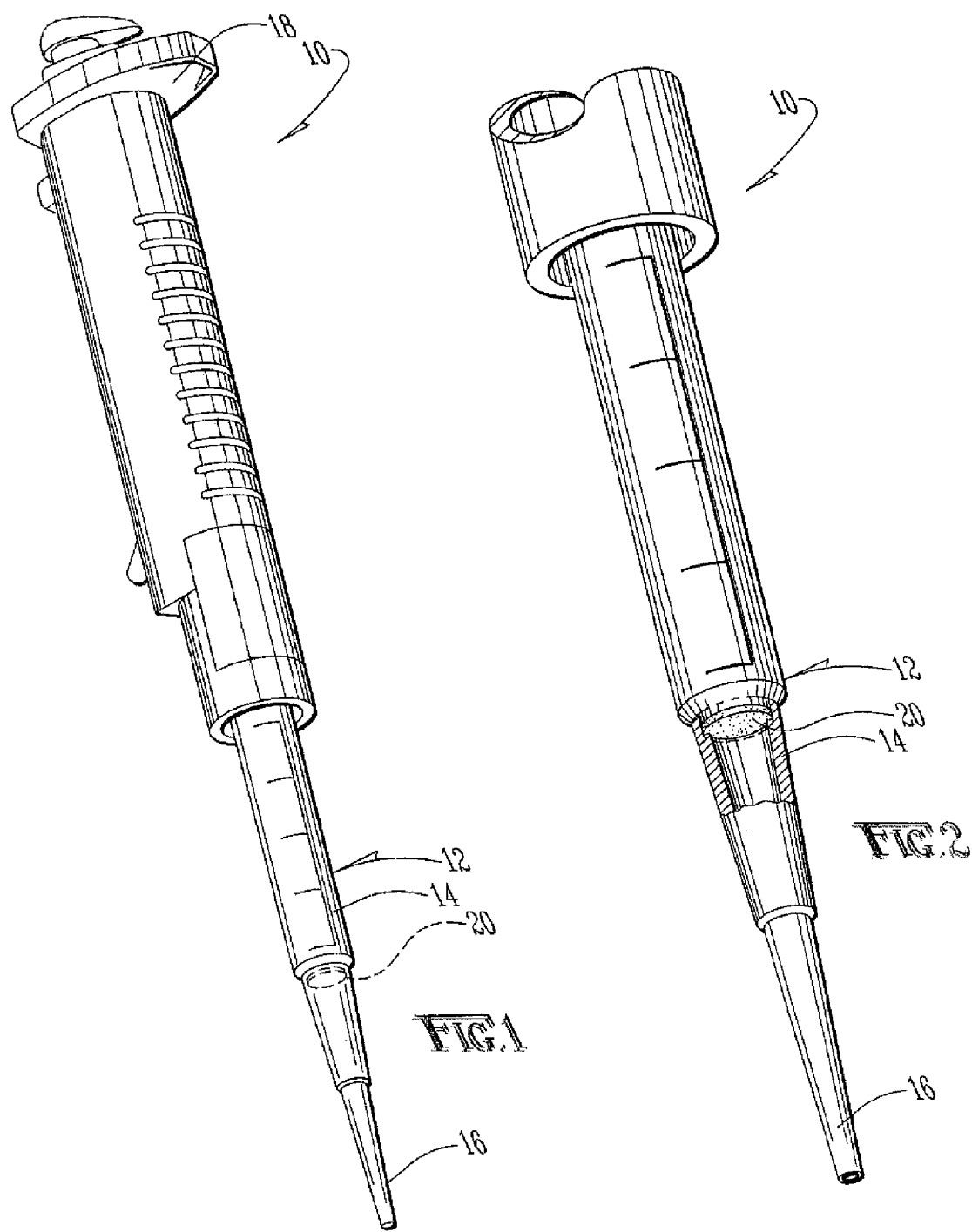

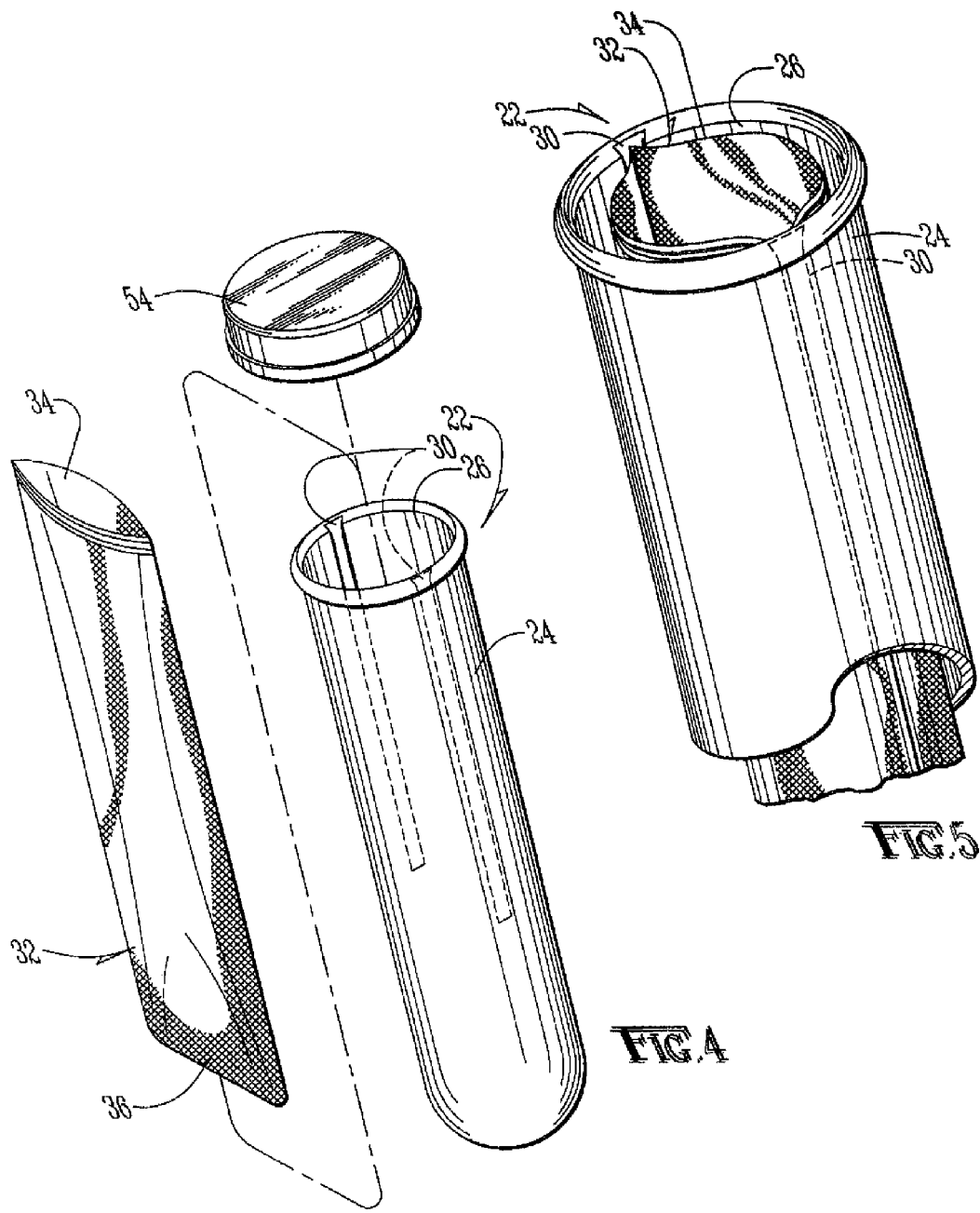

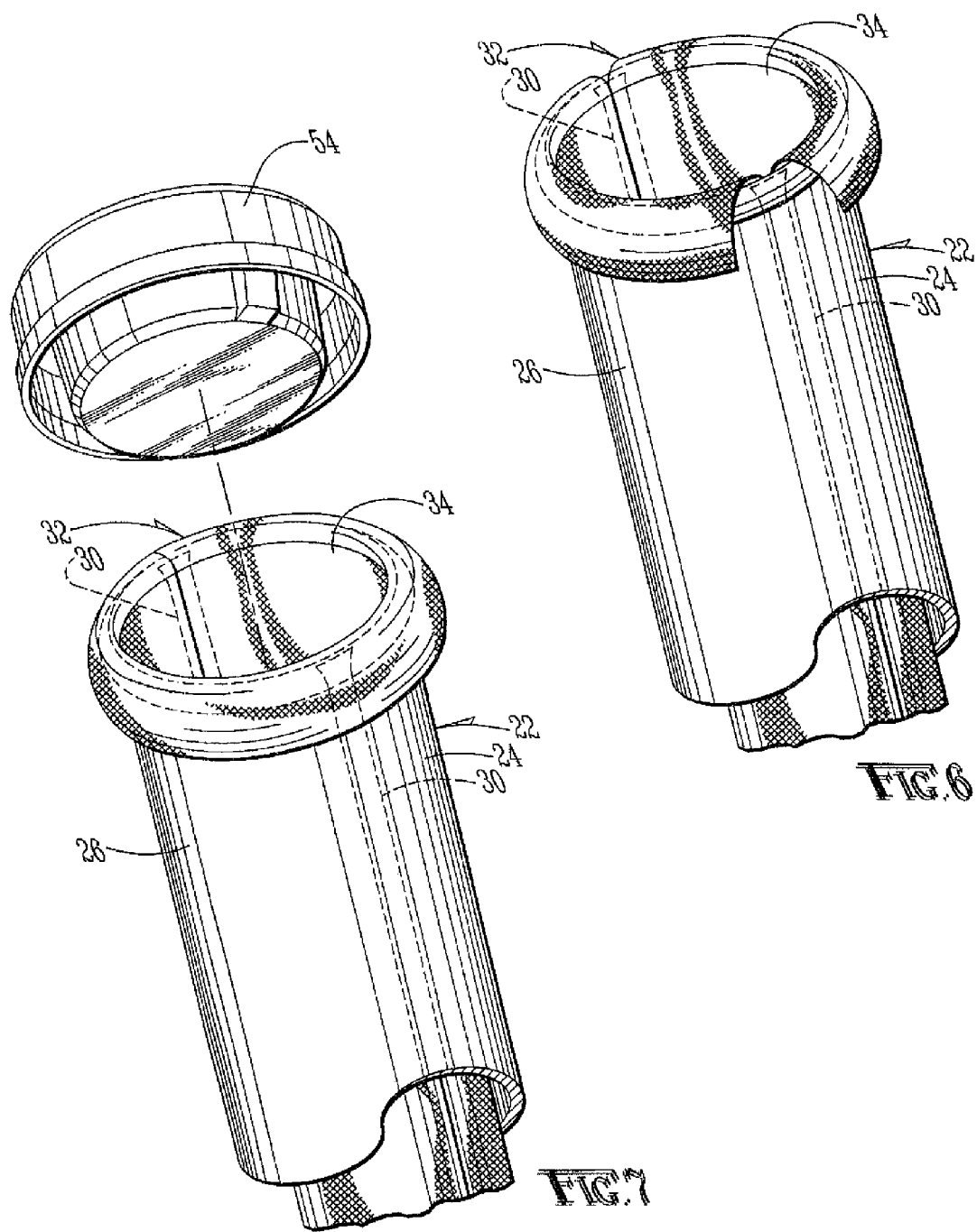

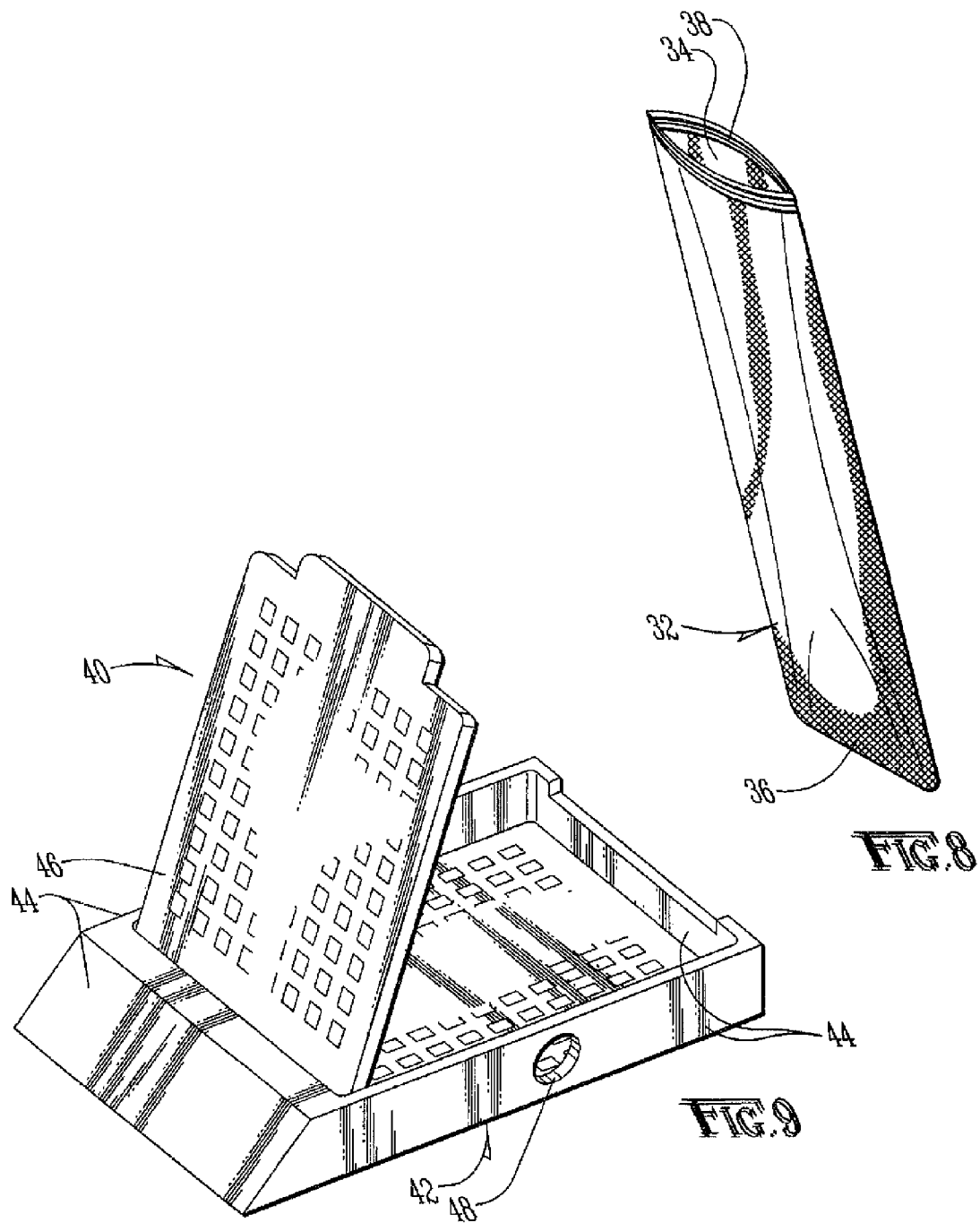

APPARATUS, SYSTEM, AND METHOD OF PROCESSING BIOPSY SPECIMEN

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

1. Field of the Invention

This invention relates generally to the art of handling of biopsy specimens, and in particular, to an apparatus, system, and method for processing biopsy specimens in preparation for analysis.

2. Description of the Related Art

Diagnosing many diseases, including cancer, requires histological analysis. Before such analysis can be performed, a biopsy is required. Biopsies are most commonly taken from the gastrointestinal tract, genitourinary tract, lung, soft tissue, and other organs. Once the tissue sample is taken, the physician places the tissue in a specimen container, typically filled with formalin. The specimen container, along with a request sheet with the patient identification and clinical information, is sent to the pathology laboratory for processing and analysis. After the container is received in the pathology laboratory, the specimen is accessioned in the pathology computer system and submitted for processing or "grossing." The grossing process begins with matching the patient identifier on the container and the corresponding request sheet. The specimen is then taken out of the container, and is placed in a labeled specimen cassette. Depending on the tissue biopsied and the suspected disease, some biopsy samples comprise multiple fragments of tissue and are very small in size. Instead of being placed in a specimen cassette, these small samples are placed in a biopsy bag. The small tissue samples can become lodged on the surface of the various instruments and containers utilized during the grossing process, including the specimen container, biopsy bag, tissue forceps, cassette, pipette, and/or the surface of a laboratory table. Each step of the grossing process is performed by a pathology assistant or a pathology resident. Based on the necessity of a person for grossing, and further because most labs do not operate 24 hours per day, the turn-around time for histological analysis of biopsy samples can be lengthy.

The prior art system also presents substantial risks of error. In a typical pathology laboratory, on average, twenty-five biopsy samples are grossed per day. Because multiple samples may be grossed at the same time, there is a risk of mislabeling the biopsy containers, placing the biopsy samples in the wrong container, or mixing and thus contaminating the samples. The applicants have also observed that on-the-job training of pathology laboratory assistants can lead to these errors in grossing.

It would therefore be desirable to develop a biopsy pipette, biopsy test tube, biopsy bag, and biopsy cassette that are capable of being utilized in a biopsy specimen processing system that will ease the method of handling biopsy samples and reduce the risk of mix-ups in processing. It would also be desirable to develop a biopsy processing system that is automated to assist pathology laboratory personnel in performing the grossing of biopsy samples, which will decrease the turn-around time for analyzing the biopsy samples and thus improve patient care.

BRIEF SUMMARY OF THE INVENTION

The present invention is directed to a biopsy pipette, biopsy test tube, biopsy bag, and biopsy cassette which may be employed in an automated biopsy specimen processing method and system.

In a first preferred embodiment, the present invention is directed to a biopsy pipette comprising a pipette, wherein said pipette comprises a wall forming an internal compartment, and a filter, wherein said filter is attached to said wall of said pipette.

In a second preferred embodiment, the present invention is directed to a biopsy test tube comprising a test tube, wherein said test tube comprises a wall forming an internal compartment, and a biopsy bag, wherein said biopsy bag is attached to said wall of said test tube.

In a third preferred embodiment, the present invention is directed to a biopsy bag comprising an open end and a closed end, wherein said open end is zip lockable.

In a fourth preferred embodiment, the present invention is directed to a biopsy cassette wherein said cassette has an opening that is configured to receive a pipette.

In a fifth preferred embodiment, the present invention is directed to a biopsy processing system comprising (a) a biopsy tissue sample, wherein said sample is in a first specimen container; (b) a biopsy pipette; (c) means for suctioning said biopsy tissue sample with said biopsy pipette from said first specimen container and dispensing said biopsy tissue sample in a second specimen container, wherein said second specimen container is porous; (d) means for placing said second specimen container in a vacuum chamber; (e) means for activating said vacuum chamber; and (f) means for removing said second specimen container from said vacuum chamber.

In a sixth preferred embodiment, the present invention is directed to a method of processing biopsy tissue samples comprising introducing a tissue sample removed from a subject into a biopsy processing system wherein said system comprises: (a) a biopsy tissue sample, wherein said sample is in a first specimen container; (b) a biopsy pipette; (c) means for suctioning said biopsy tissue sample with said biopsy pipette from said first specimen container and dispensing said biopsy tissue sample in a second specimen container, wherein said second specimen container is porous; (d) means for placing said second specimen container in a vacuum chamber; (e) means for activating said vacuum chamber; and (f) means for removing said second specimen container from said vacuum chamber.

In a seventh preferred embodiment, the present invention is directed to a biopsy processing system comprising (a) a biopsy test tube comprising a test tube, wherein said test tube comprises a wall forming an internal compartment, and a biopsy bag, wherein said biopsy bag is attached to said wall of said test tube; (b) means for placing a biopsy tissue sample in said biopsy bag; (c) means for removing said biopsy bag from said test tube; (d) means for placing said biopsy bag in a vacuum chamber; (e) means for activating said vacuum chamber; (f) means for removing said biopsy bag from said vacuum chamber; and (g) means for placing said biopsy bag in a biopsy cassette.

In an eighth preferred embodiment, the present invention is directed to a method of processing tissue biopsy samples comprising introducing a tissue sample removed from a subject into a biopsy processing system, wherein said system comprises (a) a biopsy test tube comprising a test tube, wherein said test tube comprises a wall forming an internal compartment, and a biopsy bag, wherein said biopsy bag is attached to said wall of said test tube; (b) means for placing a biopsy tissue sample in said biopsy bag; (c) means for removing said biopsy bag from said test tube; (d) means for placing said biopsy bag in a vacuum chamber; (e) means for activating said vacuum chamber; (f) means for removing said biopsy bag from said vacuum chamber; and (g) means for placing said biopsy bag in a biopsy cassette.

In a ninth preferred embodiment, the present invention is directed to a biopsy processing system comprising (a) a biopsy tissue sample, wherein said sample is in a container; (b) a biopsy cassette, wherein said cassette comprises an opening that is configured to receive a pipette; (c) means for suctioning said biopsy tissue sample with a pipette from said container; (d) means for placing said pipette in said opening of said biopsy cassette; (e) means for dispensing said biopsy specimen from said pipette to said biopsy cassette; (f) means for placing said biopsy cassette in a vacuum chamber; (g) means for activating said vacuum chamber; and (h) means for removing said biopsy cassette from said vacuum chamber.

In a tenth preferred embodiment, the present invention is directed to a method of processing biopsy tissue samples comprising introducing a tissue sample removed from a subject into a biopsy processing system, wherein said system comprises (a) a biopsy tissue sample, wherein said sample is in a container; (b) a biopsy cassette, wherein said cassette comprises an opening that is configured to receive a pipette; (c) means for suctioning said biopsy tissue sample with a pipette from said container; (d) means for placing said pipette in said opening of said biopsy cassette; (e) means for dispensing said biopsy specimen from said pipette to said biopsy cassette; (f) means for placing said biopsy cassette in a vacuum chamber; (g) means for activating said vacuum chamber; and (h) means for removing said biopsy cassette from said vacuum chamber.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

FIG. 1 is a perspective view of an embodiment of a biopsy pipette.

FIG. 2 is a perspective view of the biopsy pipette of FIG. 1.

FIG. 4 is an exploded view of a first preferred embodiment of a biopsy test tube.

FIG. 5 is a perspective view of the first preferred embodiment of the biopsy test tube of FIG. 4.

FIG. 6 is a perspective view of a second preferred embodiment of a biopsy test tube.

FIG. 7 is a perspective view of the second preferred embodiment of the biopsy test tube of FIG. 6.

FIG. 8 is a perspective view of a biopsy bag.

FIG. 9 is a perspective view of a biopsy cassette.

DETAILED DESCRIPTION OF THE INVENTION

Figure 3:
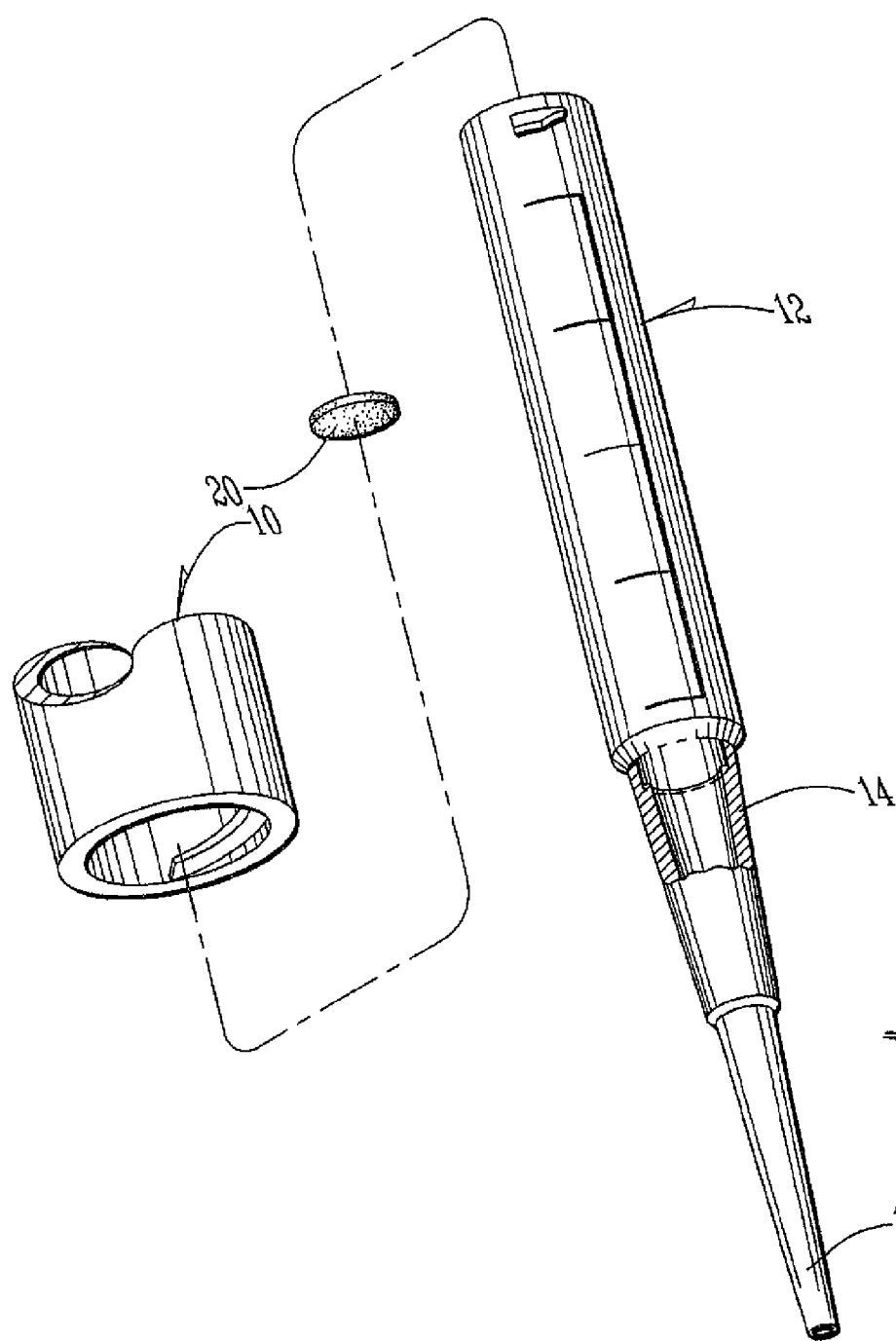
FIG. 3 is an exploded view of the biopsy pipette of FIG. 1.
Figure 10:
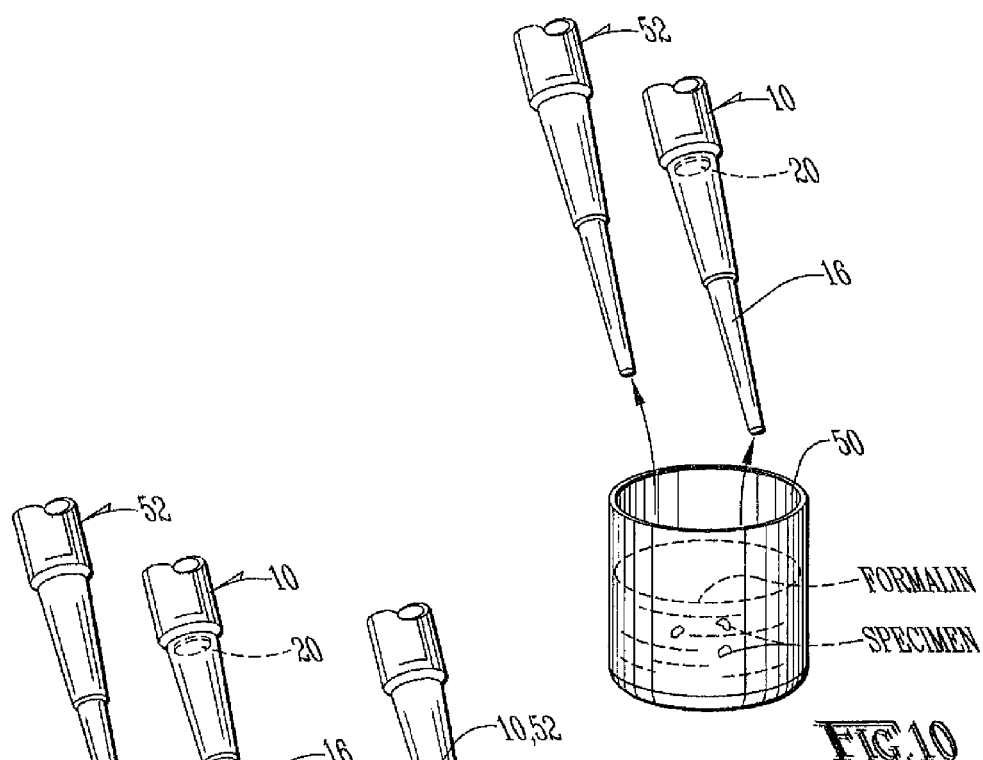
FIG. 10 is a perspective view of a biopsy pipette and biopsy container as the biopsy pipette suctions a biopsy specimen and formalin from a biopsy container.
Figure 11:
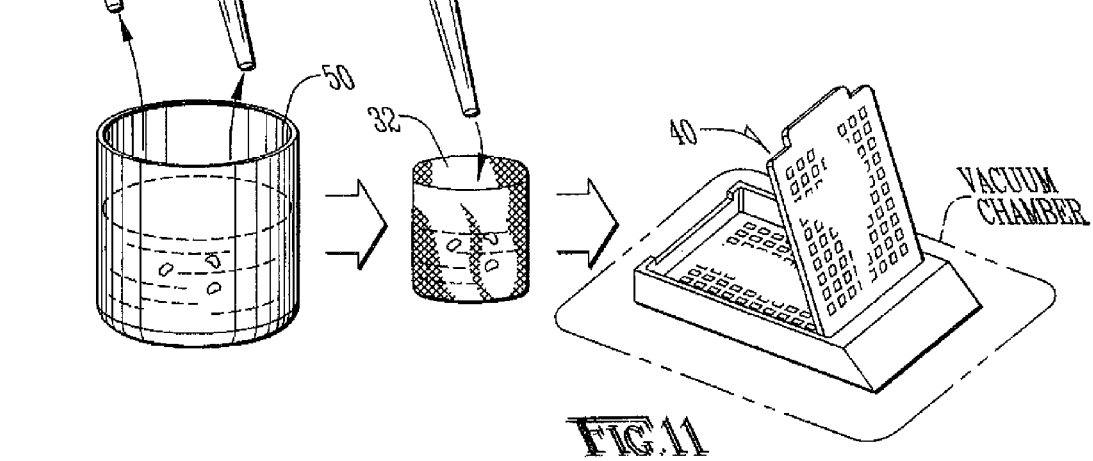
FIG. 11 is a perspective view of a biopsy pipette, biopsy container, biopsy bag, and biopsy cassette as the biopsy pipette suctions the contents of a biopsy container and then dispenses those contents into a biopsy bag, and then the biopsy bag is placed in a biopsy cassette.
Figure 12:
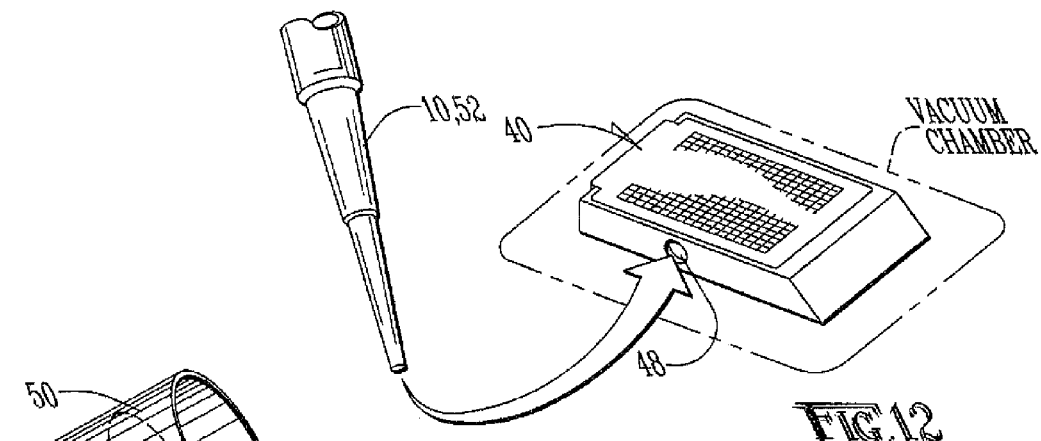
FIG. 12 is a perspective view of a biopsy pipette and biopsy cassette as the biopsy pipette dispenses its contents into the biopsy cassette.
Figure 13:
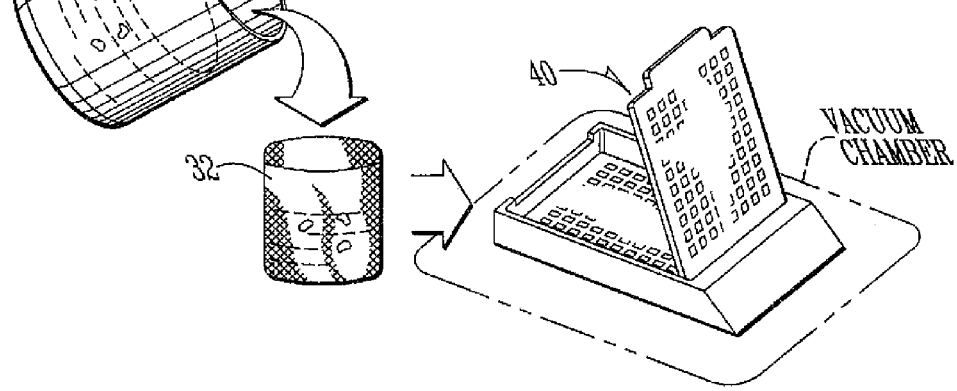
FIG. 13 is a perspective view of a biopsy container, biopsy bag, and biopsy cassette as the contents of the biopsy container are poured into the biopsy bag, and then the biopsy bag is placed into the biopsy cassette.
Figure 14:
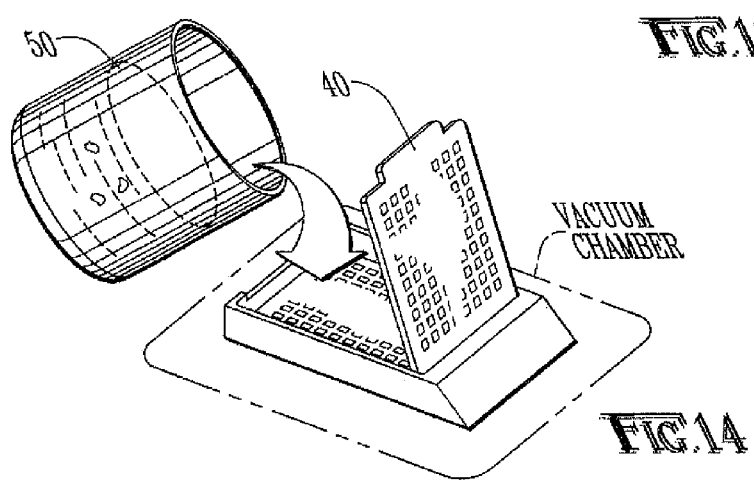
FIG. 14 is a perspective view of a biopsy container and biopsy cassette as the contents of the biopsy container are poured into the biopsy cassette.
Figure 15:
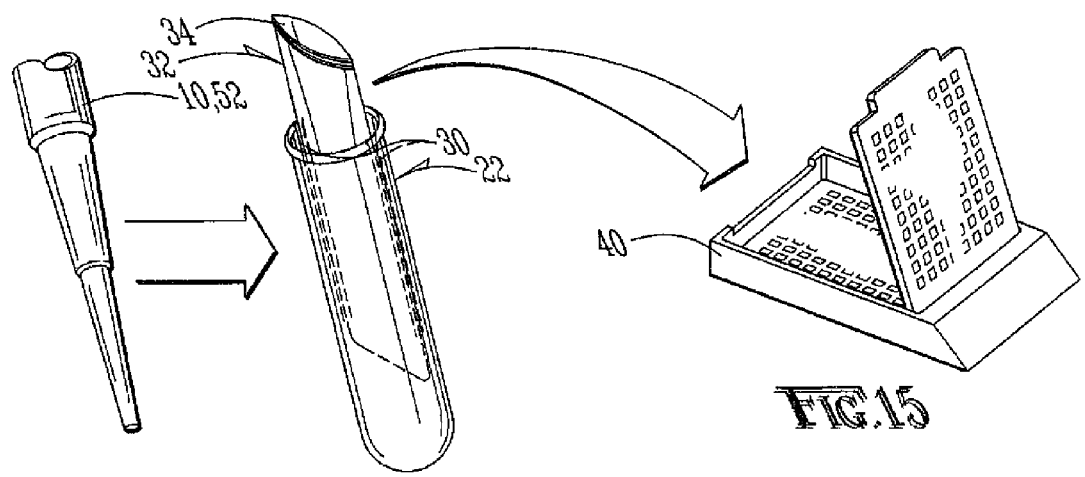
FIG. 15 is a perspective view of a biopsy pipette, biopsy test tube, and biopsy cassette as the contents of the biopsy pipette are dispensed into the biopsy bag, and then the biopsy bag is removed from the biopsy test tube and is then placed into the biopsy cassette.
Figure 16:
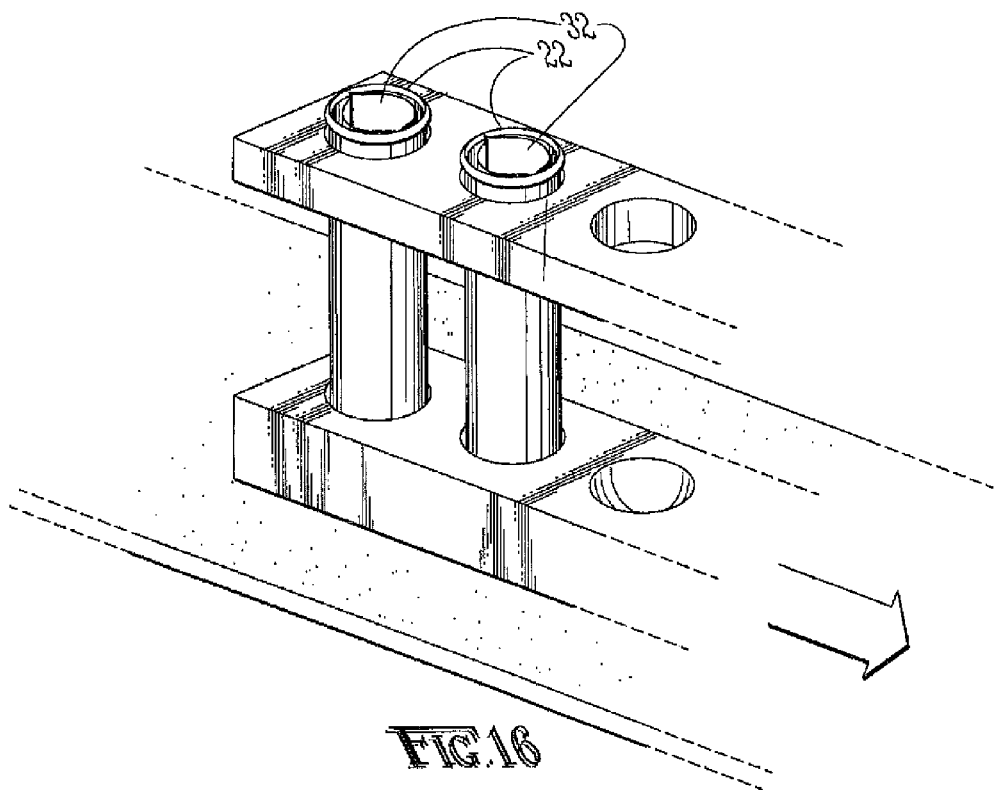
FIG. 16 is a perspective view of two biopsy test tubes in a test tube rack moving along a conveyor belt.

With reference to FIGS. 1-3, the preferred embodiments of the present invention may be described. As illustrated in FIG. 1, the biopsy pipette 10 is comprised of a pipette 12 of a kind known to those of ordinary skill in the art. The pipette 12 is preferably cylindrical in shape and comprises a wall that forms an internal compartment 14. The pipette 12 has a tip 16 on one end, and a means for suctioning and dispensing materials 18 on the other end, such as a bulb. A filter 20 is attached along its circumference to the interior surface of the wall of the pipette 12. The filter 20 is attached to the pipette 12 by means well-known to those skilled in the art. The diameter of the filter 20 will depend on the size of the pipette 12. Because biopsy tissue samples can vary in size from 1.0 mm to 1.0 cm, the pore size of the filter 20 preferably is less than 1.0 mm in size. By manipulating the bulb or other means for suctioning 18, the biopsy pipette 10 can suction the contents of a specimen container of formalin and the small fragments of tissue sample. The formalin or other liquid can pass through the filter 20, but the tissue sample cannot. When dispensing, the formalin passes back through the filter towards the tip of the pipette 10. During this passage, the formalin washes the biopsy tissue sample from its interaction with the filter 20, thus causing the release of the sample from the biopsy pipette 10.

As shown in FIGS. 4-5, the biopsy test tube 22 is comprised of a test tube 24. Test tube 24 is preferably cylindrical in shape and comprises a wall 26 that forms an internal compartment. Two grooves 30 extend longitudinally along the internal surface of the wall 26. The grooves 30 preferably are located one-half of the diameter of the test tube apart from one another. The grooves 30 are configured to receive the left and right edges of the biopsy bag 32. The biopsy bag 32 is preferably made of Tefla, or other like substances, and is preferably 0.5 cm to 2.5 cm in both length and width. The biopsy bag 32 has an open end 34 and a closed end 36. The biopsy bag 32 is also porous and displays sufficient rigidity to ensure that the bag remains completely engaged by the grooves 30, thus preventing the bag from collapsing on itself and potential lodging of a biopsy specimen in the bag. The open end of the test tube 24 is capable of receiving a cap 54. Cap 54 prevents spillage and other contamination of the biopsy sample after it is placed in the biopsy bag 32. In an alternative embodiment as shown in FIGS. 6-7, to further prevent the collapse of the biopsy bag 32 inside the test tube 24, the open end 34 of the biopsy bag 32 extends outside the open end of the test tube 24.

Thus, when the cap 54 is attached, the open end 34 of the biopsy bag 32 is secured between the cap 54 and the outside surface of the test tube 24.

In an alternative embodiment, the cap 54 has matching internal grooves 30 as those on the internal surface of the test tube wall 26. The grooves 30, extending from the cap 54 to the test tube 24, engage the left and right edges of the biopsy bag 32. In this embodiment, the cap 54 is also capable of slidably receiving an insert (not shown) in one of its sides. The insert is the same shape as the cap 54, preferably circular, square, or rectangular. When received by the cap 54, the insert extends completely through the interior of the cap 54. It therefore contacts the open end 34 of the biopsy bag 32 and forces the open end 34 to fold over itself.

The biopsy test tube 22 allows the physician to place the tissue sample directly into the biopsy bag after the biopsy is taken. As shown in FIG. 8, at the open end 34 of the bag 32 is means to zip lock 38 the bag 32 to prevent tissue contamination. After the open end 34 of the biopsy bag 32 is closed, the biopsy test tube 22 can be transported to the pathology lab for further processing. Placing the tissue sample directly into the biopsy bag prevents the possible loss or contamination of the sample that exists when the sample is first placed into a cassette or when too many pieces of tissue are placed in a cassette. For example, for proper Fluorescent In Situ Hybridization (FISH), there can be only three breast core biopsies placed in a single cassette because of the risk of overlapping. The burden therefore lies with the pathology assistant to properly identify the biopsy samples as breast biopsies, and ensure that the appropriate number of breast biopsies are removed from the specimen container and placed in each cassette. However, this burden is alleviated by the physician placing the appropriate number of biopsies in the test tube 22 at the time that they are removed. As such, the pathology assistant can simply remove the biopsy bag 32 from the biopsy test tube 22 and place the bag 32 in a cassette.

As shown in FIG. 9, the biopsy cassette 40 comprises a base 42, preferably square or rectangular, with four attached vertical walls 44. A top 46 connects to the vertical walls 44 along all four sides and is permanently hinged at one end of the cassette 46. The base 42 and the top 46 of the biopsy cassette 40 are porous. There is an opening 48 in the side of one of the vertical walls 44 that is configured to receive a pipette. The tip of the pipette may be inserted into the opening 48 of the cassette 40, and thus the suctioned materials in the pipette may be dispensed directly into the cassette 40. This feature prevents spillage or other contamination of the tissue sample that exists when the prior art cassettes are utilized. Since the diameter of the tip of the pipette ranges from 1 mm to 5 mm, the diameter of the opening 48 will likewise vary.

As shown in FIGS. 10-16, the biopsy pipette 10, the biopsy test tube 22, and the biopsy cassette 40 can be used in various combinations in the processing or grossing of biopsy specimen. In most pathology labs, biopsy tissue samples are received in a specimen container filled with formalin, and accompanied by a record identifying the patient and the sample taken. In the present invention, biopsy pipette 10 is used to aspirate or suction the small tissue samples and formalin from the specimen container 50. The filter 20 of the pipette 10 prevents the suctioned sample from passing through, however, the formalin suctioned is able to pass. When dispensing, the formalin passes back through the filter towards the tip 16 of the pipette 10. During this passage, the formalin washes the biopsy tissue sample from its interaction with the filter 20, thus causing the release of the sample from the biopsy pipette 10. As an alternative, instead of using biopsy pipette 10, any pipette 52 which would be well-known to those skilled in the art may be used.

In one preferred embodiment, the tissue sample and formalin suctioned by the pipette (10 or 52) are dispensed into a biopsy bag 32. In another preferred embodiment, the tip of the pipette (10 or 52) is inserted into the opening 48 of the biopsy cassette 40, and the tissue sample and formalin are dispensed. In yet another preferred embodiment, instead of transferring the tissue sample and formalin to the biopsy bag 32 or specimen cassette 40 by a pipette (10 or 52), the tissue sample and formalin are poured directly into the biopsy bag 32 or cassette 40.

After receiving the tissue sample and formalin, the biopsy bag 32 or cassette 40 is subjected to light negative pressure in a vacuum chamber, which causes the release of the formalin from the porous biopsy bag 32 or porous cassette 40. Alternatively, light pressure may be applied between two glass or metallic panes to cause removal of the formalin. In the method in which a biopsy bag 32 is utilized, the biopsy bag is then placed in a cassette, or alternatively, the tissue specimen is removed from the biopsy bag 32 and placed in a cassette. Once in a cassette 40, the biopsy tissue specimen is ready for further processing.

In an alternative embodiment, the physician places the tissue sample that is biopsied directly into biopsy test tube 22, which is then transported to the pathology lab. Once at the lab, the technician can remove the biopsy bag 32 from the grooves 30 of test tube 22 and place it in a specimen cassette for further processing. In this method, the step requiring the physician to first place the biopsy sample in a specimen container 50 is eliminated, thus saving time and decreasing risk for loss or contamination of the tissue sample.

In the preferred embodiments, the method and system of the present invention is completely automated using a series of robotic arms and conveyor belts, which are known to those skilled in the art. Once the specimen container 50 or the biopsy test tube 22 is received in the pathology laboratory, it is accessioned, bar coded, and placed on a conveyor belt. As the specimen container 50 or biopsy test tube 22 moves down the conveyor belt, its bar code is read by a sensor (not shown). The sensor triggers the labeling of a biopsy cassette 40 with a unique pathology identifier number. A series of robotic arms then perform the processing steps described above.

The automation of the biopsy sample processing system decreases the turn-over time for the processing and analysis of the tissue samples. The automated method and system can operate 24 hours per day without human assistance, thus allowing pathology lab personnel to devote their limited workday to analyzing the samples.

What is claimed is:

1. A method of processing biopsy tissue samples comprising the steps of:
    (a) placing a tissue sample in a first specimen container filled with a liquid;
    (b) suctioning a volume of said liquid and said tissue sample with a biopsy pipette from said first specimen container and dispensing said volume of said liquid and said tissue sample from said biopsy pipette to a second specimen container, wherein said second specimen container comprises a plurality of pores;
    (c) subjecting said second specimen container to negative pressure, thereby releasing said liquid from said second specimen container through said plurality of pores.

2. The method of claim 1 wherein said biopsy pipette comprises:
    (a) a pipette, wherein said pipette comprises a wall forming an internal compartment; and (b) a filter, wherein said filter is attached to said wall of said pipette.

3. The method of claim 1 wherein said method is automated.

4. The method of claim 1 wherein said second specimen container is a biopsy cassette.

5. The method of claim 1, wherein said second specimen container is a biopsy bag, wherein said method further comprises the step of transferring said tissue sample from said biopsy bag to a biopsy cassette.

6. A method of processing biopsy tissue samples comprising the steps of:
   (a) placing a tissue sample in a biopsy bag filled with a liquid, wherein said biopsy bag is positioned inside a test tube, wherein said biopsy bag is porous;
   (b) removing said biopsy bag from said test tube;
   (c) subjecting said biopsy bag to negative pressure, thereby releasing said liquid from said biopsy bag; and
   (d) placing said biopsy bag in a biopsy cassette.

7. The method of claim 6 wherein said method is automated.

8. A method of processing biopsy tissue samples comprising the steps of:
   (a) placing a tissue sample in a container filled with a liquid;
   (b) suctioning a volume of said liquid and said tissue sample with a biopsy pipette from said container;
   (c) placing said biopsy pipette in an opening of a biopsy cassette, wherein said biopsy cassette is porous;
   (d) dispensing said volume of said liquid and said tissue sample from said pipette to said biopsy cassette
   (e) subjecting said biopsy cassette to negative pressure, thereby releasing said liquid from said biopsy cassette.

9. The method of claim 8 wherein said method is automated.

10. The method of claim 6, wherein said test tube comprises at least one groove in a wall of said test tube for receiving said biopsy bag, wherein an open end of said biopsy bag is zip lockable.

\* \* \* \* \*